(12) United States Patent
Ueda et al.

(10) Patent No.: US 7,056,450 B2
(45) Date of Patent: Jun. 6, 2006

(54) HIGHLY CONCENTRATED AQUEOUS SOLUTIONS OF N,N-DIALKYL-GLYCINES AND PROCESS FOR PREPARATION THEREOF

(75) Inventors: Takashi Ueda, Kanagawa (JP); Makoto Saito, Kanagawa (JP); Tohru Katoh, Wakayama (JP); Katsuhisa Inoue, Wakayama (JP)

(73) Assignees: Showa Denko K.K., Tokyo (JP); Kao Corporation, Tokyo (JP)

( * ) Notice: Subject to any disclaimer, the term of this patent is extended or adjusted under 35 U.S.C. 154(b) by 0 days.

(21) Appl. No.: 10/491,717

(22) PCT Filed: Oct. 3, 2002

(86) PCT No.: PCT/JP02/10327

§ 371 (c)(1),
(2), (4) Date: Apr. 5, 2004

(87) PCT Pub. No.: WO03/031390

PCT Pub. Date: Apr. 17, 2003

(65) Prior Publication Data

US 2004/0238786 A1 Dec. 2, 2004

(30) Foreign Application Priority Data

Oct. 5, 2001 (JP) .............................. 2001-310377

(51) Int. Cl.
C07C 229/12 (2006.01)
C07C 227/42 (2006.01)
C09K 3/00 (2006.01)

(52) U.S. Cl. .................. 252/182.12; 562/554; 562/575
(58) Field of Classification Search ........... 252/182.12; 562/554, 575
See application file for complete search history.

(56) References Cited

U.S. PATENT DOCUMENTS 4,684,483 A * 8/1987 Richard et al. ............... 562/17
4,968,839 A 11/1990 Noell
6,875,890 B1 * 4/2005 Zhang ......................... 562/553

FOREIGN PATENT DOCUMENTS

| DE | 292 239 A5 | 7/1991 |
| JP | 58-34478 B2 | 7/1983 |
| JP | 63-101351 A | 5/1988 |
| JP | 2003176261 A * | 6/2003 |

OTHER PUBLICATIONS

Derwent ACC-No.: 1991-369787, patent DD 292239A, pub Jul. 25, 1991, Dietze et al.*
JPO machine translation of JP 2003176261 A (Jun. 24, 2003) Ueda et al.*
Pahal, S. et al. "An Anomalous Eschweiler-Clarke Reaction", Tetrahedron Letters, 1991, vol. 32, No. 31, pp. 3847 to 3848.
Kagaku Daijiten Henshu Iinkai, Kagaku Daijiten 4, reduced-size edtion, Kyoritsu Shuppan Co., Ltd., Oct. 15, 1963, pp. 86, 87, 516, and 517.

* cited by examiner

Primary Examiner—Matthew A. Thexton
(74) Attorney, Agent, or Firm—Sughrue Mion, PLLC

(57) ABSTRACT

An aqueous high-concentration solution of N,N-dialkylglycine, economical, easy to handle, and useful for subsequent organic chemical reactions, is provided. Also is provided a process for production thereof. The aqueous high-concentration solution of N,N-dialkylglycine which contains the N,N-dialkylglycine at a concentration of 30–80% by mass, and a metal-mineral acid salt at a content of 0.3–3% by mass can be produced industrially from an aqueous N,N-dialkylglycine alkali metal salt as the source material by the steps of
(i) neutralizing an aqueous solution of an N,N-dialkylglycine alkali metal salt with a mineral acid,
(ii) condensing the obtained aqueous solution by removal of water, and
(iii) separating by solid-liquid separation the deposited alkali metal-mineral acid salt from the resulting slurry of the aqueous N,N-dialkylglycine solution and the alkali metal-mineral acid salt.

12 Claims, No Drawings

HIGHLY CONCENTRATED AQUEOUS SOLUTIONS OF N,N-DIALKYL-GLYCINES AND PROCESS FOR PREPARATION THEREOF

TECHNICAL FIELD

The present invention relates to an aqueous high-concentration N,N-dialkylglycine solution (aqueous N,N-dialkylglycine solution of high concentration) which is useful for surfactant intermediates and medicinal and pesticidal intermediates, and relates also to a process for production thereof. The present invention facilitates industrial use of the N,N-dialkylglycine in various application fields by providing an aqueous high-concentration N,N-dialkylglycine solution.

TECHNICAL BACKGROUND

Generally, crystalline N,N-dialkylglycine is produced through synthesis of an alkali metal salt of the N,N-dialkylglycine. However, the N,N-dialkylglycine alkali metal salt has a low solubility in water. For example, N,N-dimethylglycine sodium salt has a water solubility of 25% by mass (20° C.): a higher concentration of the aqueous N,N-dimethylglycine alkali metal salt solution is not achievable. Since the aqueous N,N-dialkylglycine alkali metal salt solution cannot be prepared in a higher concentration, a storage tank for storing the aqueous solution should be larger and the expense for transportation is higher, resulting inevitably in a higher cost.

On the other hand, the preparation process of an aqueous N,N-dialkylglycine solution by dissolving crystalline N,N-dialkylglycine has disadvantages of a higher cost and much labor in crystallization and handling of the N,N-dialkylglycine. For example, the crystalline N,N-dimethylglycine can be prepared through complicated procedures including organic solvent extraction and crystallization as disclosed in U.S. Pat. No. 4,968,839. Further, the obtained N,N-dimethylglycine is extremely hygroscopic, requiring low humidity for the treatment and storage thereof, and rendering its handling more difficult.

The inventors of the present invention, after comprehensive study to solve the above problems, found that N,N-dialkylglycines have a much higher solubility in water in comparison with N,N-dialkylglycine alkali metal salts having a low solubility in water, and have completed the present invention of the aqueous high-concentration N,N-dialkylglycine solution and the process for production thereof.

The present invention intends to provide an aqueous high-concentration N,N-dialkylglycine solution which is readily handleable and economical in storage, transportation, and so forth, and is useful as a source material solution for organic chemical reactions. The present invention intends also to provide a process for production thereof.

DISCLOSURE OF THE INVENTION (1) An aqueous high-concentration solution of an N,N-dialkylglycine, produced from an N,N-dialkylglycine alkali metal salt as the source material, and containing the N,N-dialkylglycine represented by Formula (I) below:

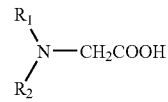

(wherein $R_1$ and $R_2$ may be the same or different and are respectively a linear alkyl or branched alkyl of 1–4 carbon atoms) at a concentration ranging from 30% to 80% by mass.

(2) The aqueous high-concentration solution of an N,N-dialkylglycine stated in the above item (1), containing an alkali metal-mineral acid salt at a concentration ranging from 0.3% to 3% by mass.

(3) An aqueous high-concentration solution of an N,N-dialkylglycine, containing the N,N-dialkylglycine represented by Formula (I) below:

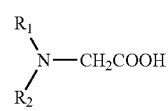

(wherein $R_1$ and $R_2$ may be the same or different and are respectively a linear alkyl or branched alkyl of 1–4 carbon atoms) at a concentration ranging from 30% to 80% by mass, and an alkali metal-mineral acid salt at a concentration ranging from 0.3% to 3% by mass.

(4) The aqueous high-concentration solution of an N,N-dialkylglycine stated in any of the above items (1)–(3), wherein $R_1$ and $R_2$ are both methyl group.

(5) The aqueous high-concentration solution of an N,N-dialkylglycine stated in any of the above items (1)–(3), wherein $R_1$ and $R_2$ are both ethyl group.

(6) A process for producing an aqueous high-concentration solution of an N,N-dialkylglycine, represented by Formula (I) below:

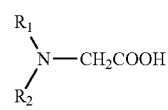

(wherein $R_1$ and $R_2$ may be the same or different and are respectively a linear alkyl or branched alkyl of 1–4 carbon atoms) at a concentration ranging from 30% to 80% by mass;

the process comprising at least the steps of (i) neutralizing an aqueous solution of an N,N-dialkylglycine alkali metal salt with a mineral acid, (ii) condensing the aqueous solution obtained in the above step by removing water, and (iii) separating by solid-liquid separation the deposited alkali metal-mineral acid salt from the resulting slurry of the aqueous N,N-dialkylglycine solution and the alkali metal-mineral acid salt in the above step.

(7) The process for producing an aqueous high-concentration solution of an N,N-dialkylglycine stated in the above item (6), wherein the N,N-dialkylglycine alkali metal salt is an N,N-dialkylglycine sodium salt.

(8) The process for producing an aqueous high-concentration solution of an N,N-dialkylglycine stated in the above item (6), wherein the mineral acid used in the step (i) is sulfuric acid.

(9) The process for producing an aqueous high-concentration solution of an N,N-dialkylglycine stated in the above item (7), wherein the mineral acid used in the step (i) is sulfuric acid.

(10) The process for producing an aqueous high-concentration solution of an N,N-dialkylglycine stated in any of the above items (6)–(9), wherein the aqueous solution is neutralized to pH 3–9 in the step (i).

(11) The process for producing an aqueous high-concentration solution of an N,N-dialkylglycine stated in any of the above items (6)–(9), wherein the solid-liquid separation in the step (iii) is conducted at a temperature ranging from 10° C. to 80° C.

(12) The process for producing an aqueous high-concentration solution of an N,N-dialkylglycine stated in any of the above items (6)–(9), wherein the separated alkali metal-mineral acid salt is washed with water to recover the N,N-dialkylglycine adhering to the alkali metal-mineral acid salt.

(13) The process for producing an aqueous high-concentration solution of an N,N-dialkylglycine stated in item (12), wherein the resulting water after washing of the alkali metal-mineral acid salt is added to the solution or slurry prior to the above step (i) and/or (ii) to recover the N,N-dialkylglycine adhering to the alkali metal-mineral acid salt.

MODE FOR CARRYING OUT THE INVENTION

The present invention provides an aqueous high-concentration solution of an N,N-dialkylglycine, containing the N,N-dialkylglycine represented by Formula (I) below:

(wherein $R_1$ and $R_2$ may be the same or different and are respectively a linear alkyl or branched alkyl of 1–4 carbon atoms) at a concentration ranging from 30% to 80% by mass, and a process for production thereof.

In the process of the present invention, the aqueous N,N-dialkylglycine alkali metal salt solution is neutralized with a mineral acid and is condensed to deposit a mineral acid salt with allowing the most portion of the N,N-dialkylglycine to be kept dissolved, and the mineral acid salt is removed by solid-liquid separation to obtain the aqueous high-concentration N,N-dialkylglycine solution. The obtained aqueous high-concentration N,N-dialkylglycine solution contains the alkali metal-mineral acid salt formed from the mineral acid and the source material employed for the neutralization at a salt concentration ranging from 0.3% to 3% by mass.

The substituents $R_1$ and $R_2$ in the N,N-dialkylglycine represented by the above Formula (I) may be the same or different, and are preferably a linear alkyl or a branched alkyl of 1–4 carbon atoms, respectively. The compound includes specifically, N,N-dimethylglycine, N-ethyl-N-methylglycine, N,N-diethylglycine, N-isopropyl-N-methylglycine, N-isopropyl-N-ethylglycine, N,N-diisopropylglycine, N,N-dibutylglycine, N-butyl-N-methylglycine, and N-butyl-N-ethylglycine, but is not limited thereto.

The N,N-dialkylglycine has an extremely high solubility in water, which enables preparation of an aqueous solution at a concentration of as high as 80% by mass or more at or around the neutral point. However, the aqueous solution of the concentration higher than 80% by mass has a high viscosity, being not suitable as a source material for synthesis and for other uses. On the other hand, the aqueous solution having a concentration lower than 30% by mass is disadvantageous in the use of N,N-dialkylglycine in a subsequent synthesis or other uses because of the low concentration as the source material ascribable to difficulty in removal of water. At the concentration of 30% by mass or lower of the N,N-dialkylglycine, the solubilities of the mineral acid salt and impurities are higher, whereby the purity of the aqueous N,N-dialkylglycine solution is lowered. Therefore, the concentration of the aqueous high-concentration solution of N,N-dialkylglycine is preferably in the range of 30–80% by mass, more preferably from 50–80% by mass in consideration of use or handling as the source material in organic chemical reaction.

The concentration of the alkali metal-mineral acid salt remaining unremoved in the aqueous high-concentration N,N-dialkylglycine solution varies with the concentration of the N,N-dialkylglycine as described above as well as the type of mineral acid and the kind of alkali metal of the N,N-dialkylglycine alkali metal salt. The acceptable concentration of the remaining alkali metal-mineral acid salt depends on the use in synthesis reactions and other application fields, and may be decided in consideration of the labor and cost for decreasing the amount of the remaining salt and for raising the purity of the aqueous high-concentration solution of the N,N-dialkylglycine. Generally the acceptable concentration of the remaining salt is desirably not higher than 3% by mass, preferably 0.3–3% by mass, more preferably 0.3–2.5% by mass, still more preferably 0.7–2.3% by mass.

The aqueous N,N-dialkylglycine alkali metal salt solution as the source material for producing the aqueous high-concentration N,N-dialkylglycine solution of the invention may be prepared in any process without limitation. The process is exemplified by production of N,N-dialkylglycine sodium salt by the reaction of bromoacetic acid with a dialkylamine (Japanese Patent Publication 58-34478); production of N,N-dimethylglycine sodium salt by the reaction of formalin, sodium cyanide, and a dialkylamine in the presence of sodium hydrogensulfite to obtain an N,N-dimethylacetonitrile as an intermediate for the N,N-dimethylglycine sodium salt, and hydrolysis of the intermediate by an alkali metal (U.S. Pat. No. 4,968,839); production of N,N-dialkylglycine sodium salt by the reaction of a dialkylamine, formalin, and sodium cyanide under alkaline conditions by Strecker reaction (DD Patent 292239); and so forth.

The process for producing the aqueous high-concentration N,N-dialkylglycine solution of the present invention comprises at least the steps of (i) neutralizing an aqueous solution of an N,N-dialkylglycine alkali metal salt with a mineral acid, (ii) condensing the resulting aqueous solution in the above step(i) by removing water, and (iii) separating by solid-liquid separation, the deposited alkali metal-mineral acid salt from the resulting slurry of the aqueous N,N-dialkylglycine solution and the alkali metal-mineral acid salt in the above step, to produce an aqueous high-concentration solution of the N,N-dialkylglycine represented by Formula (I) below:

(wherein $R_1$ and $R_2$ may be the same or different and are respectively a linear alkyl or branched alkyl of 1–4 carbon atoms) at a concentration ranging from 30% to 80% by mass.

This process gives an aqueous high-concentration N,N-dialkylglycine solution containing the N,N-dialkylglycine at a concentration of 30–80% by mass, together with the alkali metal-mineral acid salt at a concentration of 0.3–3% by mass.

In the process for producing the aqueous high-concentration N,N-dialkylglycine solution of the present invention, the steps (i) and (ii) are conducted to obtain a slurry containing the aqueous N,N-dialkylglycine solution and the alkali metal-mineral acid salt, and followed by the step (iii). In this process, firstly, an aqueous N,N-dialkylglycine alkali metal salt solution as the source material is subjected to the step (i) of neutralization of the N,N-dialkylglycine alkali metal salt with a mineral acid and the step (ii) of condensation by removing water from the resulting aqueous solution. The steps (i) and (ii) are usually conducted in this order preferably. However, the step (ii) may be firstly conducted, and thereafter the step (i) may follow. Otherwise, the steps (i) and (ii) may be repeatedly conducted.

Thus, a slurry comprising the aqueous N,N-dialkylglycine solution and the alkali metal-mineral acid salt is yielded through the steps (i) and (ii) for treating the aqueous N,N-dialkylglycine alkali metal salt solution. Next, the aqueous high-concentration N,N-dialkylglycine solution is obtained by conducting the step (iii) of solid-liquid separation of the deposited alkali metal-mineral acid salt from the slurry of the aqueous N,N-dialkylglycine solution and the alkali metal-mineral acid salt. After this step (iii), further the steps (i), (ii), and (iii) may be repeatedly conducted, as necessary.

According to the process for producing an aqueous high-concentration N,N-dialkylglycine solution of the present invention, the aqueous solution of the N,N-dialkylglycine of a high concentration can be obtained without isolating the N,N-dialkylglycine as a pure solid from the N,N-dialkylglycine alkali metal salt. In other words, the present invention provides N,N-dialkylglycine in a form of a source material solution usable, as it is, as a synthesis intermediate without requiring a step of preparing the solid crystal thereof for subsequent synthesis process.

The aqueous N,N-dialkylglycine alkali metal salt solution as the source material includes aqueous solutions of salts of sodium, potassium, and lithium. Of these, sodium salts are particularly preferred in view of the cost and the solubility of the mineral acid salts in the later step.

In the step (i), a mineral acid is used as an acid for neutralization. The mineral acid includes sulfuric acid, hydrochloric acid, nitric acid, and phosphoric acid. Of these acids, sulfuric acid is preferred in consideration of the solubility and other properties of the resulting alkali metal-mineral acid salt. Therefore, the mineral acid salt is particularly preferably a combination of sulfuric acid and sodium, namely sodium sulfate.

In the neutralization, the pH is brought within the range of 3–9. At a higher pH, the N,N-dialkylglycine alkali metal salt will deposit in the condensation step, whereas at a lower pH, a part of the sodium sulfate may be converted to sodium hydrogensulfate having a higher solubility to deteriorate the quality of the aqueous N,N-dialkylglycine solution. The pH is more preferably in the range of 5–8. In the case where the steps (i) and (ii) are repeated, the final pH is preferably adjusted within this range.

The condensation of the solution by removal of water in the step (ii) may be conducted according to any known method. For example, evaporation by heating under a reduced pressure is convenient. This condensation operation allows the formed mineral acid salt to deposit whereby the solution becomes a slurry state. The content of the N,N-dialkylglycine in the slurry after the condensation is adjusted appropriately in consideration of the required concentration of the aqueous N,N-dialkylglycine solution and the acceptable concentration of the alkali metal-mineral acid salt as an impurity in the later synthesis. The concentration of the N,N-dialkylglycine in the aqueous solution after removal of the alkali metal-mineral acid salt is preferably in the range of 30–80% by mass. At a concentration of the N,N-dialkylglycine of lower than 30% by mass, the concentration of the alkali metal-mineral acid salt in the resulting aqueous solution will be higher, not lower than 3% by mass any longer, whereas at a concentration of the N,N-dialkylglycine higher than 80% by mass, the slurry viscosity will be higher, which makes difficult the solid-liquid separation in the following step. Therefore the concentration is preferably in the range of 30–80% by mass.

The present invention utilizes the fact that N,N-dialkylglycines have a solubility in water much higher than that of the N,N-dialkylglycine alkali metal salts. No N,N-dialkylglycine crystal will deposit even with condensation to a high extent, and resultingly an aqueous high-concentration N,N-dialkylglycine solution is formed. Moreover, the solubility of alkali metal-mineral acid salt formed in neutralization of the N,N-dialkylglycine alkali metal salt with the mineral acid is decreased owing to a kind of salting-out effect with increase of the N,N-dialkylglycine concentration. This facilitates formation of the aqueous N,N-dialkylglycine solution of high purity after the solid-liquid separation. The solid-liquid separation in the step (iii) may be conducted by any conventional solid-liquid separation means, as exemplified by filtration with a filter such as a Buchner funnel, and separation by centrifugation.

The aforementioned solid-liquid separation is conducted preferably at a temperature within the range of 10–80° C., but the temperature is not limited thereto. At a temperature higher than 80° C., the solubility of the mineral acid salt increases with the temperature, so that the dissolved impurities increase, lowering the quality of the aqueous N,N-dialkylglycine solution. On the other hand, at a temperature lower than 10° C., the viscosity of the aqueous N,N-dialkylglycine solution is higher, which requires a longer time for the separation of the alkali metal-mineral acid salt. Therefore the separation is conducted more favorably at a temperature within the range of 30–70° C.

The concentration of the aqueous high-concentration N,N-dialkylglycine solution after the solid-liquid separation depends on the degree of the condensation. The concentration may be adjusted by addition of water as necessary to a desired concentration. The concentration is preferable in the range of 30–80% by mass as mentioned above. In consideration of the use for synthesis reactions and ease of handling, the concentration is preferable in the range of 40–80% by mass, more preferably 50–80% by mass.

The alkali metal-mineral acid salt separated in the above step (iii) holds adhering or occuluded water which contains the N,N-dialkylglycine dissolved therein. This N,N-dialkylglycine adhering to the separated alkali metal-mineral acid salt can be recovered by washing the alkali metal-mineral acid salt with water, by adding the resultant wash water containing the N,N-dialkylglycine to the aqueous N,N-dialkylglycine alkali metal salt solution or to the slurry constituted of the aqueous N,N-dialkylglycine solution and the alkali metal-mineral acid salt before or during the step (i). and/or the step (ii) of the next repetition, and by conducting the subsequent step. Thereby, the recovery rate of the N,N-dialkylglycine can be increased.

The operations of condensation, separation, washing, and recovery of the washing solution may be conducted consecutively or separately. In the production process of the present invention, the setup of the steps including the order, repetition, and recovery, and the conditions such as the concentration of the aqueous N,N-dialkylglycine solution, the amount of remaining alkali metal-mineral acid salt and so forth are suitably adjusted to meet the application fields and the necessity.

EXAMPLES

The present invention is described more specifically by reference to Examples without intention limiting the invention in any way.

In the production process described below, deionized water was used as the process water.

Reference Example 1

An aqueous 20% by mass solution of N,N-dimethylglycine sodium salt which had been synthesized from dimethylamine, formalin, and sodium cyanide by Strecker reaction was condensed at 80° C. under a reduced pressure. The condensation was continued until the concentration of the N,N-dimethylglycine sodium salt reached 30% by mass. The aqueous 30% by mass solution of N,N-dimethylglycine sodium salt thus obtained was left standing at room temperature. Thereby, crystalline N,N-dimethylglycine sodium salt deposited. The solubility of the N,N-dimethylglycine sodium salt in water was found to be 25% by mass (20° C.)

Example 1

To 20 kg of an aqueous 20% by mass solution of the N,N-dimethylglycine sodium salt which had been synthesized in the same manner as in Reference Example 1, was added 95% by mass sulfuric acid to adjust the pH of the solution to 5.0. The resulting aqueous solution was condensed at 80° C. under a reduced pressure until the N,N-dimethylglycine concentration reached 60% by mass. The condensed solution was cooled to 50° C. and stirred for one hour. The deposited crystalline sodium sulfate was removed by centrifugation. Thereby, an aqueous 60% by mass solution of N,N-dimethylglycine was obtained in an amount of 4.7 kg. The aqueous N,N-dimethylglycine solution contained sodium sulfate at a concentration of 2.3% by mass.

Example 2

To 20 kg of an aqueous 20% by mass solution of the N,N-dimethylglycine sodium salt which had been synthesized in the same manner as in Reference Example 1, was added 95% by mass sulfuric acid to adjust the pH of the solution to 7.0. The resulting aqueous solution was condensed at 80° C. under a reduced pressure until the N,N-dimethylglycine concentration reached 65% by mass. The condensed solution was cooled to 50° C. and stirred for one hour. Deposited crystalline sodium sulfate was removed by centrifugation. Thereby, an aqueous 65% by mass solution of N,N-dimethylglycine was obtained in an amount of 4.3 kg. The aqueous N,N-dimethylglycine solution contained sodium sulfate at a concentration of 1.2% by mass. To the aqueous 65% by mass solution of N,N-dimethylglycine, pure water was added to yeild an aqueous 60% by mass solution of N,N-dimethylglycine. This aqueous solution was left standing at 0° C. for 10 days, but no crystalline deposit was observed.

Example 3

To 20 kg of an aqueous 20% by mass solution of N,N-dimethylglycine sodium salt which had been synthesized in the same manner as in Reference Example 1, was added 95% by mass sulfuric acid to adjust the pH of the solution to 7.0. The aqueous solution was condensed at 80° C. under a reduced pressure until the N,N-dimethylglycine concentration reached 70% by mass. The condensed solution was cooled to 50° C. and stirred for one hour. The deposited crystalline sodium sulfate was removed by centrifugation. Thereby, an aqueous 70% by mass solution of N,N-dimethylglycine was obtained in an amount of 4.0 kg. The aqueous N,N-dimethylglycine solution contained sodium sulfate at a concentration of 0.7% by mass. To the aqueous 70% by mass solution of N,N-dimethylglycine, pure water was added to obtain an aqueous 60% by mass solution of N,N-dimethylglycine. This aqueous solution was left standing at 0° C. for 10 days, but no crystalline deposit was observed.

Example 4

To 20 kg of an aqueous 20% by mass solution of N,N-dimethylglycine sodium salt which had been synthesized in the same manner as in Reference Example 1, was added 95% by mass sulfuric acid to adjust the pH of the solution to 7.0. Separately, the crystalline sodium sulfate taken out in Example 2 was washed with an equal weight of water. The thus obtained wash water was mixed with the above solution having the pH adjusted to 7.0 by addition of sulfuric acid. This mixture was condensed at 80° C. under a reduced pressure until the N,N-dimethylglycine concentration reached 65% by mass. The condensed solution was cooled to 50° C. and stirred for one hour. The deposited crystalline sodium sulfate was removed by centrifugation. Thereby, an aqueous 60% by mass solution of N,N-dimethylglycine was obtained in an amount of 4.9 kg. The aqueous N,N-dimethylglycine solution contained sodium sulfate at a concentration of 1.2% by mass. The washed sodium sulfate contained N,N-dimethylglycine at a content of 0.6% by mass.

Example 5

Powdery solid N,N-diethylglycine sodium salt (produced by Tokyo Kasei Kogyo K.K. Japan) was dissolved in deionized water. The solubility in water of the N,N-diethylglycine sodium salt was 34% by mass (20° C.). To 342 g of this aqueous 34% by mass solution, was added 98% by mass sulfuric acid to adjust the pH to 6.6. This aqueous solution was condensed at 90° C. under a reduced pressure until the N,N-diethylglycine sodium salt concentration in the solution reached 67% by mass. The condensed solution was cooled to 40° C. and was stirred for one hour. The deposited crystalline sodium sulfate was removed at 40° C. by using a Buchner vacuum filter. Thereby, an aqueous 67% by mass solution of N,N-diethylglycine was obtained in an amount of 125 g. The aqueous N,N-diethylglycine solution contained sodium sulfate at a concentration of 0.9% by mass.

Example 6

To 342 g of the aqueous 34% by mass solution of N,N-diethylglycine which had been prepared in the same manner as in Example 5, was added 98% by mass sulfuric acid to adjust the pH to 5.0. This aqueous solution was condensed at 80° C. under a reduced pressure until the N,N-diethylglycine sodium salt concentration in the solution reached 67% by mass. The condensed solution was cooled to 60° C. and was stirred for one hour. The deposited crystalline sodium sulfate was removed at this temperature by using a Buchner vacuum filter. Thereby, an aqueous 67% by mass solution of N,N-diethylglycine was obtained in an amount of 121 g. The aqueous N,N-diethylglycine solution contained sodium sulfate at a concentration of 0.9% by mass.

The aqueous high-concentration solution of dialkylglycine of the present invention enables reduction of the cost of storage and transportation. This aqueous high-concentration solution of N,N-dialkylglycine is convenient for use as the source material for a synthesis reaction in comparison with crystalline N,N-dialkylglycine.

The high-concentration solution of the N,N-dialkylglycine can be used, as it is, in a next synthesis process. Thereby the reaction efficiency is improved and the productivity is increased.

The invention claimed is:

1. An aqueous high-concentration solution of an N,N-dialkylglycine, produced from an N,N-dialkylglycine alkali metal salt as the source material, and containing the N,N-dialkylglycine represented by Formula (I) below:

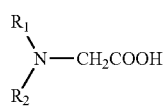

at a concentration ranging from 50% to 80% by mass, wherein $R_1$ and $R_2$ may be the same or different and are respectively a linear alkyl or branched alkyl of 1–4 carbon atoms.

2. The aqueous high-concentration solution of an N,N-dialkylglycine according to claim 1, containing an alkali metal-mineral acid salt at a concentration ranging from 0.3% to 3% by mass.

3. The aqueous high-concentration solution of an N,N-dialkylglycine according to any of claims 1 to 2, wherein $R_1$ and $R_2$ are both methyl group.

4. The aqueous high-concentration solution of an N,N-dialkylglycine in any of claims 1 to 2, wherein $R_1$ and $R_2$ are both ethyl group.

5. A process for producing an aqueous high-concentration solution of an N,N-dialkylglycine comprising at least the steps of
(i) neutralizing an aqueous solution of an N,N-dialkylglycine alkali metal salt with a mineral acid,
(ii) condensing the aqueous solution obtained in the above step by removing water to yield a slurry, and
(iii) separating by solid-liquid separation the deposited alkali metal-mineral acid salt from the resulting slurry of the aqueous N,N-dialkylglycine solution and the alkali metal-mineral acid salt in the above step to obtain the aqueous high concentration solution of N,N-dialkylglycine represented by Formula (I) below:

at a concentration ranging from 50% to 80% by mass, wherein $R_1$ and $R_2$ may be the same or different and are respectively a linear alkyl or branched alkyl of 1–4 carbon atoms.

6. The process for producing an aqueous high-concentration solution of an N,N-dialkylglycine according to claim 5, wherein the N,N-dialkylglycine alkali metal salt is an N,N-dialkylglycine sodium salt.

7. The process for producing an aqueous high-concentration solution of an N,N-dialkylglycine according to claim 5, wherein the mineral acid used in the step (i) is sulfuric acid.

8. The process for producing an aqueous high-concentration solution of an N,N-dialkylglycine according to claim 6, wherein the mineral acid used in the step (i) is sulfuric acid.

9. The process for producing an aqueous high-concentration solution of an N,N-dialkylglycine according to any of claims 5 to 8, wherein the aqueous solution is neutralized to pH 3 to 9 in the step (i).

10. The process for producing an aqueous high-concentration solution of an N,N-dialkylglycine according to any of claims 5 to 8, wherein the solid-liquid separation in the step (iii) is conducted at a temperature ranging from 10° C. to 80° C.

11. The process for producing an aqueous high-concentration solution of an N,N-dialkylglycine according to any of claims 5 to 8, wherein the separated alkali metal-mineral acid salt is washed with water to recover the N,N-dialkylglycine adhering to the alkali metal-mineral acid salt.

12. The process for producing an aqueous high-concentration solution of an N,N-dialkylglycine according to claim 11, wherein the resulting water after washing of the alkali metal-mineral add salt is added to the solution or slurry prior to the above step (i) and/or (ii) to recover the N,N-dialkylglycine adhering to the alkali metal-mineral acid salt.

* * * * *